(12) United States Patent
Kramer et al.

(10) Patent No.: US 9,751,900 B2
(45) Date of Patent: *Sep. 5, 2017

(54) HYDROXYSILANE AND POLYMER CONTAINING SILANE GROUPS

(71) Applicant: SIKA TECHNOLOGY AG, Baar (CH)

(72) Inventors: Andreas Kramer, Zürich (CH); Urs Burckhardt, Zürich (CH); Ursula Stadelmann, Zürich (CH)

(73) Assignee: SIKA TECHNOLOGY AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/891,819

(22) PCT Filed: May 21, 2014

(86) PCT No.: PCT/EP2014/060457
§ 371 (c)(1),
(2) Date: Nov. 17, 2015

(87) PCT Pub. No.: WO2014/187865
PCT Pub. Date: Nov. 27, 2014

(65) Prior Publication Data
US 2016/0102110 A1    Apr. 14, 2016

(30) Foreign Application Priority Data

May 22, 2013 (EP) .................... 13168803

(51) Int. Cl.
| | | |
|---|---|---|
| *C07F 7/08* | (2006.01) |
| *C08G 18/83* | (2006.01) |
| *C08G 77/26* | (2006.01) |
| *C07F 7/18* | (2006.01) |
| *C08G 18/48* | (2006.01) |
| *C08G 18/75* | (2006.01) |
| *C08G 18/10* | (2006.01) |

(52) U.S. Cl.
CPC .......... *C07F 7/0834* (2013.01); *C07F 7/1836* (2013.01); *C07F 7/1872* (2013.01); *C08G 18/10* (2013.01); *C08G 18/4866* (2013.01); *C08G 18/755* (2013.01); *C08G 18/837* (2013.01); *C08G 77/26* (2013.01)

(58) Field of Classification Search
CPC .. C08G 18/10; C08G 18/289; C08G 18/2875; C08G 18/837; C08G 18/755; C08G 77/26; C07F 7/0834; C07F 7/1836; C07F 7/1872

See application file for complete search history.

(56) References Cited

U.S. PATENT DOCUMENTS

| | | | |
|---|---|---|---|
| 2,946,701 A * | 7/1960 | Plueddemann | C03C 25/40 166/295 |
| 5,587,502 A | 12/1996 | Moren et al. | |
| 8,049,027 B2 | 11/2011 | Honma et al. | |
| 2010/0099866 A1 | 4/2010 | Honma et al. | |
| 2013/0281562 A1 | 10/2013 | Burckhardt | |

FOREIGN PATENT DOCUMENTS

| | | |
|---|---|---|
| EP | 2180001 A1 | 4/2010 |
| EP | 2468759 A1 | 6/2012 |
| JP | 2004-161846 A | 6/2004 |
| WO | 96/38453 A1 | 12/1996 |

OTHER PUBLICATIONS

Jul. 2, 2014 Search Report issued in International Patent Application No. PCT/EP2014/060457.
Apr. 25, 2017 Office Action issued in Chinese Patent Application No. 201480029544.9.

* cited by examiner

*Primary Examiner* — Christopher M Rodd
(74) *Attorney, Agent, or Firm* — Oliff PLC

(57) ABSTRACT

Special hydroxysilanes, which can be obtained by reacting β-(3,4-epoxycyclohexyl)alkyltrialkoxysilanes with secondary amines, and adducts of the hydroxysilanes in the form of polymers containing silane groups. The hydroxysilanes can be produced having high purity in a simple process and are very stable in storage after production. The polymers containing silane groups that can be obtained by means of the hydroxysilanes have advantageous properties. The polymers enable moisture-curing compositions, which contain no isocyanate groups and which are suitable as elastic adhesives and sealants.

12 Claims, No Drawings

HYDROXYSILANE AND POLYMER CONTAINING SILANE GROUPS

TECHNICAL FIELD

The invention relates to hydroxysilanes and to the use thereof in curable compositions.

PRIOR ART

Organosilanes having a functional group are often used in sealants, adhesives and coatings. They are used, inter alia, as adhesion promoters or crosslinkers, and as formation components for preparation of polymers containing silane groups, also called "silane-functional polymers" or "silane-terminated polymers" or "STP". An easily performable and commercially attractive route to polymers containing silane groups leads via polyurethane polymers containing isocyanate groups, which are reacted with suitable organosilanes. Most commonly used for this purpose are aminosilanes. However, polymers thus prepared typically have high viscosities and/or limited thermal stability because of the urea groups formed in the reaction with the aminosilane.

Better properties in relation to viscosity and thermal stability are possessed by polymers containing silane groups in which the silane groups are bonded to the polymer via urethane rather than urea groups. Such systems are known in the form of reaction products of polyols and isocyanatosilanes. However, this route is only of limited commercial interest, since isocyanatosilanes are costly, have low storage stability and are highly toxic. A more attractive alternative in principle is the reverse route to polymers containing silane groups and having urethane bonds, namely via the reaction of polyurethane polymers containing isocyanate groups with hydroxysilanes. However, there have barely been any descriptions to date of such polymers. This is because the preparation of suitable hydroxysilanes usually presents difficulties, because they have a tendency to self-condense owing to a rapid reaction of the hydroxyl group with the silane group and are therefore frequently very impure and/or have low storage stability.

U.S. Pat. No. 5,587,502 discloses silanes having hydroxyl groups, obtained by reacting aminosilanes with cyclic alkylene carbonates, and polymers containing silane groups that originate therefrom. These polymers containing silane groups have unsatisfactory thermal stabilities.

U.S. Pat. No. 8,049,027 discloses addition products of glycidyl ether epoxysilanes with secondary amines, forming mixtures of cyclic siloxanes, hydroxysilanes and oligomeric condensates thereof. These hydroxysilanes are unsuitable for the preparation of high-quality polymers containing silane groups, since they are not pure enough.

SUMMARY OF THE INVENTION

It is therefore an object of the present invention to provide a hydroxysilane which is preparable in high purity and has good storage stability, such that it is especially possible to obtain polymers containing silane groups with good thermal stability.

It has been found that, surprisingly, this object is achieved by a hydroxysilane as claimed in claim 1. It is preparable in a simple process in very high purity and has excellent storage stability, even with methoxy groups on the silicon, which are very reactive and hence particularly prone to self-condensation. Methoxy-functional silanes, because of their high reactivity, are of particular interest as a constituent of curable compositions.

As well as other advantageous uses, it is possible to use the hydroxysilane as claimed in claim 1 to obtain, in a simple process proceeding from polyurethane polymers containing isocyanate groups, low-viscosity polymers containing silane groups and having good storage stability, which cure rapidly with moisture to give an elastic material having good strength, extensibility and thermal stability.

Further aspects of the invention are the subject of further independent claims. Particularly preferred embodiments of the invention are the subject of the dependent claims.

WAYS OF EXECUTING THE INVENTION

The invention provides a hydroxysilane of the formula (I)

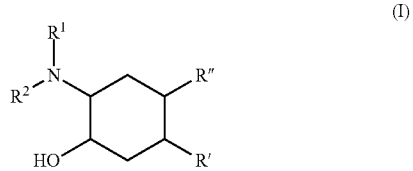

where
either R' is a radical of the formula (II) and R" is hydrogen or R' is hydrogen and R" is a radical of the formula (II);

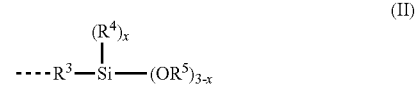

$R^1$ and $R^2$
  are either each individually an alkyl radical having 1 to 12 carbon atoms and optionally having heteroatoms in the form of ether oxygen, thioether sulfur or tertiary amine nitrogen,
  or together are an alkylene radical having 2 to 12 carbon atoms and optionally having heteroatoms in the form of ether oxygen, thioether sulfur or tertiary amine nitrogen;
$R^3$ is a linear or branched alkylene or cycloalkylene radical having 1 to 20 carbon atoms, optionally having aromatic moieties, and optionally having one or more heteroatoms;
$R^4$ is an alkyl group having 1 to 8 carbon atoms;
$R^5$ is an alkyl group having 1 to 10 carbon atoms and optionally having one or more ether oxygen heteroatoms; and
x is 0 or 1 or 2.

In the present document, the term "silane" or "organosilane" refers to compounds which firstly have at least one alkoxy group, typically two or three alkoxy groups, bonded directly to the silicon atom via Si—O bonds, and secondly at least one organic radical bonded directly to the silicon atom via an Si—C bond.

"Silane group" refers to the silicon-containing group bonded to the organic radical of a silane.

"Aminosilane", "hydroxysilane", "isocyanatosilane" and the like refer to organosilanes having a corresponding functional group, i.e. an amino group, hydroxyl group or isocyanate group, on the organic radical.

Substance names beginning with "poly", such as polyol or polyisocyanate, refer to substances which, in a formal sense, contain two or more of the functional groups that occur in their name per molecule.

The term "polyurethane polymer" encompasses all polymers which are prepared by what is called the diisocyanate polyaddition process. The term "polyurethane polymer" also encompasses polyurethane polymers having isocyanate groups, as obtainable from the reaction of polyisocyanates and polyols, which are themselves polyisocyanates and are often also called prepolymers.

"Molecular weight" in the present document is understood to mean the molar mass (in grams per mole) of a molecule. "Mean molecular weight" is understood to mean the number average $M_n$ of an oligomeric or polymeric mixture of molecules, which is typically determined by means of GPC against polystyrene as standard.

A dotted line in the formulae in this document represents the bond between a substituent and the corresponding remainder of the molecule in each case.

The term "storage-stable" refers to the property of a substance or composition that it can be kept at room temperature in a suitable container over several weeks to 6 months or more without any change in the application or use properties thereof that results from the storage to a degree of relevance for its use.

"Room temperature" refers to a temperature of about 23° C.

The hydroxysilane of the formula (I) corresponds either to the formula (I a) or to the formula (I b).

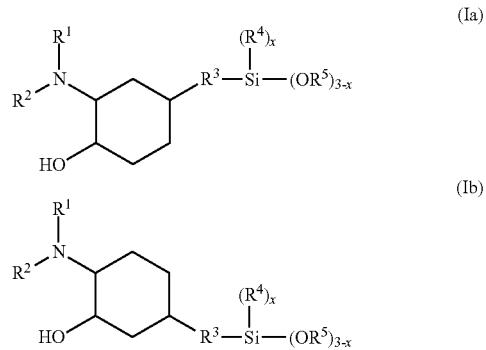

In the formulae (I a) and (I b), $R^1$, $R^2$, $R^3$, $R^4$, $R^5$ and x are each as already defined.

The formulae (I a) and (I b) encompass all the diastereomers possible for the respective structures.

Preferably, $R^1$ and $R^2$
are either each individually an alkyl radical having 3 to 10 carbon atoms and optionally having one or two ether oxygens,
or together are an alkylene radical having 4 to 8 carbon atoms and especially having a heteroatom in the form of ether oxygen, thioether sulfur or tertiary amine nitrogen and form, with inclusion of the nitrogen atom shown in formula (I), a 5- or 6- or 7-membered ring, especially a 5- or 6-membered ring.

More preferably, $R^1$ and $R^2$
are either individually 2-methoxyethyl, 2-ethoxyethyl, 3-methoxypropyl, 3-ethoxypropyl, 2-(2-methoxyethoxy)ethyl, 2-octyloxyethyl, ethyl, propyl, isopropyl, butyl, isobutyl, sec-butyl, 2-ethylhexyl, or N,N-dimethylaminopropyl,
or together with inclusion of the nitrogen atom are an optionally substituted pyrrolidine, piperidine, hexamethyleneimine, morpholine, thiomorpholine or 4-methylpiperazine ring.

Even more preferably, $R^1$ and $R^2$ are each individually 2-methoxyethyl, butyl or isopropyl, or together with inclusion of the nitrogen atom are morpholine, 2,6-dimethylmorpholine, thiomorpholine, pyrrolidine or 4-methylpiperazine.

Most preferably, $R^1$ and $R^2$ with inclusion of the nitrogen atom are morpholine or pyrrolidine.

These hydroxysilanes are preparable in particularly pure quality and are particularly storage-stable. They enable polymers containing silane groups with good thermal stability.

$R^3$ is preferably a linear or branched alkylene radical having 1 to 6 carbon atoms, more preferably an ethylene radical.

$R^4$ is preferably a methyl group.

$R^5$ is preferably a methyl group or an ethyl group or a hept-3,6-dioxa-1-yl group, more preferably a methyl group or an ethyl group.

Hydroxysilanes having these preferred $R^3$, $R^4$ and $R^5$ radicals have particularly good obtainability.

$R^5$ is especially a methyl group. These hydroxysilanes are particularly reactive with moisture. In this way, polymers containing silane groups with particularly rapid curing are obtainable.

$R^5$ is additionally especially an ethyl group. These hydroxysilanes do not eliminate any methanol in the course of curing, which is advantageous for toxicological reasons.

Preferably, x is 1 or 0, especially 0. These hydroxysilanes are hydrolyzed particularly rapidly on contact with moisture and enable polymers containing silane groups with particularly good mechanical properties.

The invention further provides a process for preparing a hydroxysilane of the formula (I) by reacting at least one epoxysilane of the formula (III) with at least one amine of the formula (IV).

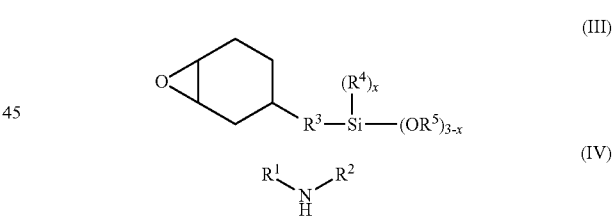

In the formulae (III) and (IV), $R^1$, $R^2$, $R^3$, $R^4$, $R^5$ and x are each as already defined.

The amine of the formula (IV) can be added onto the carbon in the β or γ position to the silane group, giving rise either to a hydroxysilane of the formula (I a) in which the silane radical is in the 4 position based on the hydroxyl group, or to a hydroxysilane of the formula (I b) in which the silane radical is in the 5 position based on the hydroxyl group. This process typically affords mixtures of the two hydroxysilanes of the formula (I a) and (I b).

The reaction is preferably conducted at temperatures in the range from 50 to 140° C., especially 70 to 120° C. In the reaction, it is possible to use a catalyst, especially an imidazole, a hydroxyalkylamine, an alcohol, a phenol, a Brønsted acid such as, in particular, acetic acid or methanesulfonic acid, a Lewis acid such as, in particular, aluminum (III) acetylacetonate, aluminum(III) isopropoxide, alumnum(III) ethoxide, lanthanum(III) triflate, zinc dichloride or zinc bis(ethylhexanoate), or a metal salt such as, in particular, sodium dodecylsulfate or lithium perchlorate. The amine of the formula (IV) is preferably used in a slightly superstoichiometric or stoichiometric ratio to the epoxysilane of the formula (III). More particularly, an amine/epoxysilane ratio in the range from 1.3 to 1.0 is employed. The reaction can be effected without solvent or in a suitable solvent. Preferably, after the reaction, any volatile compounds present, especially solvents, unreacted reactants or methanol or ethanol released, are removed from the reaction product by distillation.

In the preferred process for preparing the hydroxysilane of the formula (I), it is formed especially in a purity of at least 90% by weight, preferably at least 95% by weight. The high purity of the hydroxysilane of the formula (I) is particularly surprising, given that hydroxysilanes according to the prior art typically have contents of impurities of more than 10% by weight.

The epoxy silane of the formula (III) used is preferably a β-(3,4-epoxycyclo-hexyl)ethyltrialkoxysilane. Particularly suitable products are β-(3,4-epoxycyclo-hexyl)ethyltrimethoxysilane, commercially available, for example, as Silquest® A-186 from Momentive, and additionally β-(3,4-epoxycyclohexyl)ethyltriethoxysilane, commercially available, for example, as Coatosil®-1770 from Momentive.

Suitable amines of the formula (IV) are especially bis(2-methoxyethyl)amine, bis(2-ethoxyethyl)amine, bis(3-methoxypropyl)amine, bis(3-ethoxypropyl)-amine, bis(2-(2-methoxyethoxy)ethyl)amine, bis(2-octyloxyethyl)amine, diethylamine, dipropylamine, diisopropylamine, dibutylamine, diisobutylamine, di-sec-butylamine, di-2-ethylhexylamine, N-methylbutylamine, N-ethylbutyl-amine, bis(3-(N,N-dimethylamino)propyl)amine, pyrrolidine, piperidine, 2-methylpiperidine, hexamethyleneimine (=azepane), morpholine, 2,6-dimethylmorpholine, thiomorpholine and 4-methylpiperazine.

Among these, preference is given to bis(2-methoxyethyl)amine, dibutylamine, diisopropylamine, morpholine, 2,6-dimethylmorpholine, thiomorpholine, pyrrolidine and 4-methylpiperazine. Most preferred are morpholine and pyrrolidine.

With these amines, particularly pure hydroxysilanes of the formula (I) are obtained and the hydroxysilanes are particularly storage-stable.

Particularly preferred hydroxysilanes of the formula (I) are 2-bis(2-methoxy-ethyl)amino-4-(2-triethoxysilylethyl)cyclohexan-1-ol, 2-dibutylamino-4-(2-triethoxysilylethyl)cyclohexan-1-ol, 2-diisopropylamino-4-(2-triethoxysilyl-ethyl)-cyclohexan-1-ol, 2-morpholino-4-(2-triethoxysilylethyl)cyclohexan-1-ol, 2-(2,6-dimethylmorpholino)-4-(2-triethoxysilylethyl)cyclohexan-1-ol, 2-thiomorpholino-4-(2-triethoxysilylethyl)cyclohexan-1-ol, 2-pyrrolidino-4-(2-triethoxysilylethyl)-cyclohexan-1-ol, 2-(4-methylpiperazino)-4-(2-triethoxysilylethyl)cyclohexan-1-ol and the corresponding compounds in which the silane radical is in the 5 position rather than in the 4 position, and the corresponding compounds having methoxy groups rather than ethoxy groups on the silane.

Mixtures of two compounds wherein the silane radical is in the 4 position or in the 5 position are also represented by the notation "4(5)". A mixture of 2-morpholino-4-(2-triethoxysilylethyl)cyclohexan-1-ol and 2-morpholino-5-(2-triethoxysilylethyl)cyclohexan-1-ol is also referred to as "2-morpholino-4(5)-(2-trimethoxysilylethyl)cyclohexan-1-ol".

Most preferred are 2-morpholino-4-(2-trimethoxysilylethyl)cyclohexan-1-ol, 2-morpholino-4-(2-triethoxysilylethyl)cyclohexan-1-ol, 2-pyrrolidino-4-(2-trimethoxysilylethyl)cyclohexan-1-ol and 2-pyrrolidino-4-(2-triethoxysilylethyl)-cyclohexan-1-ol and the corresponding compounds in which the silane radical is in the 5 position rather than in the 4 position.

Particular preference is given in each case to a mixture of the two molecules having the silane radical in the 4 position and in the 5 position, i.e. 2-morpholino-4(5)-(2-trimethoxysilylethyl)cyclohexan-1-ol, 2-morpholino-4(5)-(2-triethoxysilylethyl)cyclohexan-1-ol, 2-pyrrolidino-4(5)-(2-trimethoxysilylethyl)cyclohexan-1-ol and 2-pyrrolidino-4(5)-(2-triethoxysilylethyl)cyclohexan-1-ol.

Preference is given to the ethoxysilanes. The hydrolysis thereof releases ethanol, which is advantageous for toxicological reasons.

The hydroxysilane of the formula (I) is very storage-stable with exclusion of moisture. At room temperature, barely any decrease in purity is found over a period of several months, and not just for those having ethoxy groups but surprisingly also for hydroxysilanes containing methoxy groups of the formula (I), which are much more reactive.

The fundamental difficulty in preparing and storing hydroxysilanes is that a hydroxyl group can react with a silane group to release the alcohol $R^5$—OH ("self-condensation"). This is possible in principle either via an intramolecular or intermolecular route, giving rise either to cyclic silanes or to more highly condensed or oligomeric silane compounds having a plurality of silicon atoms. Such impurities can already arise during the preparation of hydroxysilanes or during storage.

The silane groups of the hydroxysilane of the formula (I) have the property of being hydrolyzed on contact with moisture. This forms organosilanols (organosilicon compounds containing one or more silanol groups, Si—OH groups) and, by subsequent condensation reactions, organosiloxanes (organosilicon compounds containing one or more siloxane groups, Si—O—Si groups), releasing the corresponding alcohol, for example ethanol in the case of ethoxy groups on the silicon.

The—at least partial—hydrolysis of at least one hydroxysilane of the formula (I) affords compounds having at least one silanol group of the formula (V).

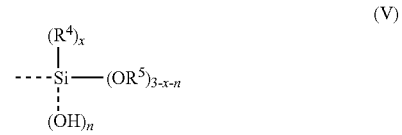

In the formula (V), n is 1 or 2 or 3, with the proviso that the maximum value of n is (3−x). $R^4$, $R^5$ and x are each as already defined.

Such hydrolyzed or partially hydrolyzed compounds having silanol groups of the formula (V) are very reactive and can react further very rapidly, either by condensation with further silanol groups to form siloxane groups (Si—O—Si groups) or, for example, by condensation with hydroxyl groups of a substrate. The hydroxysilane of the formula (I) has the ability to build up strong adhesion to various substrates, or to improve the adhesion of compositions comprising this silane to a substrate.

The hydroxysilane of the formula (I) can advantageously be used for preparation of adducts. This is done by reacting it with at least one compound containing at least one group, preferably at least two groups, reactive toward hydroxyl groups.

The invention further provides an adduct obtained from the reaction of a hydroxysilane of the formula (I) with at least one compound having at least one reactive group, preferably at least two reactive groups, selected from the group consisting of isocyanate, epoxide, acryloyl, methacryloyl, anhydride, carboxylic acid, ester, carbonate and cyclocarbonate groups.

Among these, preference is given to isocyanate, anhydride, carboxylic acid, ester, carbonate and cyclocarbonate groups.

Particular preference is given to compounds having isocyanate groups.

The reaction can be conducted in such a way that the hydroxysilane of the formula (I) is used stoichiometrically or in a stoichiometric excess relative to the reactive groups mentioned, it being possible to obtain adducts having at least one silane group, preferably at least two silane groups, which are substantially free of the reactive groups mentioned.

The reaction can alternatively be conducted in such a way that the reactive groups are present in a stoichiometric excess over the hydroxysilane of the formula (I).

The reaction between the hydroxysilane of the formula (I) and the compounds having reactive groups is effected under known conditions as typically used for reactions between the reactive groups involved in the particular reaction. The reaction is effected using a solvent or preferably without solvent. It is optionally possible to additionally use auxiliaries, for example catalysts, initiators, desiccants or stabilizers. The reaction with isocyanate groups is preferably effected at elevated temperature, for example at 40 to 100° C., and in the presence of at least one suitable catalyst.

Particularly suitable compounds having isocyanate groups are monomeric and/or oligomeric aliphatic, cycloaliphatic, arylaliphatic or aromatic polyisocyanates, especially hexamethylene 1,6-diisocyanate, 1-isocyanato-3,3,5-trimethyl-5-isocyanatomethylcyclohexane, diphenylmethane 4,4'-, 2,4'- and 2,2'-diisocyanate and tolylene 2,4- and 2,6-diisocyanate; oligomers of these isocyanates containing uretdione, isocyanurate or iminooxadiazinedione groups; modified polyisocyanates containing ester, urea, urethane, biuret, allophanate, carbodiimide, uretonimine or oxadiazinetrione groups; and polyurethane polymers having isocyanate groups, i.e. reaction products of polyisocyanates with polyols that have more than one isocyanate group, such as, in particular, polyhydric alcohols, glycols or amino alcohols, polyhydroxy-functional polyethers, polyesters, polyacrylates, polycarbonates or polyhydrocarbons, especially polyethers as mentioned hereinafter for preparation of polyurethane polymers containing isocyanate groups; and also isocyanatosilanes such as, in particular, 3-isocyanatopropyltrimethoxysilane and 3-isocyanatopropyltriethoxy-silane.

The—at least partial—hydrolysis of such adducts gives rise to compounds having silanol groups of the formula (V), just as described for the hydroxysilanes of the formula (I). Such hydrolyzed or partially hydrolyzed adducts are very reactive and can react further very rapidly, in the same way as described previously.

Both the hydroxysilane of the formula (I) and adducts thereof are advantageously usable as adhesion promoters between polymers and various substrates, for coating surfaces, for example in order to improve the properties thereof with regard to tendency to soiling, ease of cleaning, etc.,
and/or as drying agent. For this purpose, they can be used as such or as a constituent of solutions or compositions, for example as a pre-treatment composition or activator, or primer.

Suitable substrates for use as an adhesion promoter or for coating of the surfaces thereof are especially the substrates S1 and S2 mentioned hereinafter.

It is particularly advantageous to use a hydroxysilane of the formula (I) or an adduct thereof as constituent of a curable composition. The curable composition is especially a polyurethane composition having isocyanate groups, an epoxy resin composition or a composition having silane groups. Curable compositions of this kind can especially be used as potting compounds, sealants, adhesives, coverings, coatings and paints for construction and industrial applications.

Preferably, the curable composition is an elastic adhesive and/or sealant.

The curable composition may additionally be an activator or a primer typically comprising at least one solvent and optionally further constituents such as, in particular, catalysts, further silanes, titanates and zirconates, and optionally fillers, wetting agents, polyisocyanates, polyurethane polymers having isocyanate and/or silane groups, or epoxy resins.

The aforementioned uses of the hydroxysilane of the formula (I) or an adduct thereof give rise to an article. This article is especially a built structure in construction or civil engineering or an industrial good.

The invention further provides a polymer which has end groups of the formula (VI) and is free of isocyanate groups and is an adduct of a hydroxysilane of the formula (I).

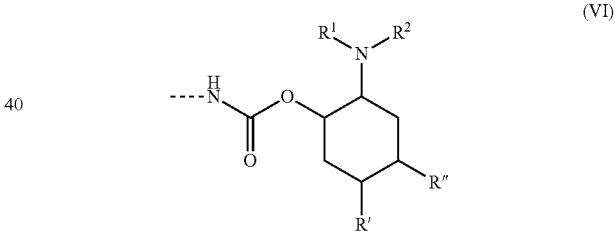

In the formula (VI), R', R'', $R^1$, $R^2$, $R^3$, $R^4$, $R^5$ and x are each as already defined.

Preferably, the polymer having end groups of the formula (VI) has a molecular weight in the range from 1,000 to 30,000 g/mol, preferably 2,000 to 25,000 g/mol, more preferably 3,000 to 20,000 g/mol, and especially from 4,000 to 15,000 g/mol. Such a polymer enables good mechanical properties. Preferably, the polymer having end groups of the formula (VI) has a majority of polyoxyalkylene units, more preferably polyoxyethylene and/or polyoxypropylene units, especially polyoxypropylene units. Such a polymer has a low viscosity and enables good mechanical properties, especially good elasticity, even at low temperatures.

The majority of the end groups of the formula (VI) are especially bonded to cycloaliphatic radicals. Such a polymer has particularly good light stability and stability to discoloration.

Preferably, the polymer has 1 to 4, more preferably 1 to 3, especially 2 or 3 and most preferably 2 end groups of the formula (VI). Such a polymer enables good mechanical properties, especially high extensibility.

The polymer having end groups of the formula (VI) is especially obtained by the reaction of at least one hydroxysilane of the formula (I) with at least one polyurethane polymer containing isocyanate groups.

In this reaction, the hydroxyl groups are used at least in a stoichiometric ratio, preferably in a slightly superstoichiometric ratio, relative to the isocyanate groups. More particularly, an OH/NCO ratio of 1.0 to 1.25 is used. The reaction is preferably conducted at a temperature in the range from 20° C. to 120° C., especially 50° C. to 100° C. Preference is given to using at least one catalyst, especially a bismuth(III), zinc(II), zirconium(IV) or tin(II) compound or an organotin compound.

For reaction with at least one polyurethane polymer containing isocyanate groups, the hydroxysilane of the formula (I) is preferably selected from the group consisting of 2-bis(2-methoxyethyl)amino-4-(2-triethoxysilylethyl)cyclohexan-1-ol, 2-dibutylamino-4-(2-triethoxysilylethyl)cyclohexan-1-ol, 2-diisopropylamino-4-(2-triethoxysilylethyl)cyclohexan-1-ol, 2-morpholino-4-(2-triethoxysilylethyl)cyclohexan-1-ol, 2-(2,6-dimethylmorpholino)-4-(2-triethoxy-silylethyl)cyclohexan-1-ol, 2-thiomorpholino-4-(2-triethoxysilylethyl)cyclohexan-1-ol, 2-pyrrolidino-4-(2-triethoxysilylethyl)cyclohexan-1-ol, 2-(4-methylpiperazino)-4-(2-triethoxysilylethyl)cyclohexan-1-ol and the corresponding compounds in which the silane radical is in the 5 position rather than in the 4 position, and the corresponding compounds having methoxy groups rather than ethoxy groups on the silane.

Among these, particular preference is given to 2-morpholino-4-(2-trimethoxy-silylethyl)cyclohexan-1-ol, 2-morpholino-4-(2-triethoxysilylethyl)cyclohexan-1-ol, 2-pyrrolidino-4-(2-trimethoxysilylethyl)cyclohexan-1-ol and 2-pyrrolidino-4-(2-triethoxysilylethyl)cyclohexan-1-ol and the corresponding compounds in which the silane radical is in the 5 position rather than in the 4 position.

Most preferred in each case are a mixture of the molecule having the silane radical in the 4 and 5 positions, i.e. 2-morpholino-4(5)-(2-trimethoxysilylethyl)-cyclohexan-1-ol, 2-morpholino-4(5)-(2-triethoxysilylethyl)cyclohexan-1-ol, 2-pyrrolidino-4(5)-(2-trimethoxysilylethyl)cyclohexan-1-ol and 2-pyrrolidino-4(5)-(2-triethoxysilylethyl)cyclohexan-1-ol.

With these hydroxysilanes, polymers having low viscosity and good storage stability are obtained, which cure rapidly with moisture to give crosslinked polymers of high strength, extensibility and good thermal stability.

A suitable polyurethane polymer containing isocyanate groups for this reaction is especially obtained by reaction of at least one polyol with at least one polyisocyanate, especially a diisocyanate. This reaction can be effected by reacting the polyol and the polyisocyanate by customary methods, especially at temperatures of 50° C. to 100° C., optionally with additional use of suitable catalysts, with metered addition of the polyisocyanate in such a way that the isocyanate groups thereof are present in a stoichiometric excess in relation to the hydroxyl groups of the polyol. More particularly, the excess of polyisocyanate is chosen such that, in the resulting polyurethane polymer, after the reaction of all the hydroxyl groups in the polymer, there remains a content of free isocyanate groups of 0.1% to 5% by weight, preferably 0.1% to 2.5% by weight, more preferably 0.2% to 1% by weight, based on the overall polymer. Preference is given to polyurethane polymers having said content of free isocyanate groups that are obtained from the reaction of diisocyanates with high molecular weight diols in an NCO/OH ratio of 1.5/1 to 2.2/1, especially 1.8/1 to 2.0/1. If necessary, the polyurethane polymer can be prepared with additional use of plasticizers, in which case the plasticizers used do not contain any groups reactive toward isocyanates.

Suitable polyols for the preparation of a polyurethane polymer containing isocyanate groups are especially the following commercially available polyols or any desired mixtures thereof:

polyoxyalkylene polyols, also called polyether polyols or oligoetherols, which are polymerization products of ethylene oxide, 1,2-propylene oxide, 1,2- or 2,3-butylene oxide, oxetane, tetrahydrofuran or mixtures thereof, possibly polymerized with the aid of a starter molecule having two or more active hydrogen atoms, for example water, ammonia or compounds having a plurality of OH or NH groups, for example ethane-1, 2-diol, propane-1,2- and -1,3-diol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, cyclohexane-1,3- and -1,4-dimethanol, bisphenol A, hydrogenated bisphenol A, 1,1,1-trimethylolethane, 1,1,1-trimethylolpropane, glycerol, aniline, and mixtures of the aforementioned compounds. Preference is given to polyoxyalkylenepolyols having a low degree of unsaturation (measured to ASTM D-2849-69 and reported in milliequivalents of unsaturation per gram of polyol (meq/g)), prepared, for example, with the aid of what are called double metal cyanide complex catalysts (DMC catalysts).

Particularly suitable are polyoxyalkylenediols or polyoxyalkylenetriols, especially polyoxyethylene- and polyoxypropylenedi- and -triols.

Also particularly suitable are what are called ethylene oxide-terminated (EO-endcapped) polyoxypropylenepolyols. The latter are mixed polyoxyethylene-polyoxypropylene polyols which are obtained, for example, by further alkoxylating polyoxypropylene polyols with ethylene oxide on completion of the polypropoxylation reaction and have primary hydroxyl groups as a result.

Styrene-acrylonitrile- or acrylonitrile-methyl methacrylate-grafted polyether polyols.

Polyester polyols, also called oligoesterols, prepared by known processes, especially for polycondensation of hydroxycarboxylic acids or for polycondensation of aliphatic and/or aromatic polycarboxylic acids with di- or polyhydric alcohols.

Especially suitable polyester polyols are those prepared from di- to trihydric, especially dihydric, alcohols, for example ethylene glycol, diethylene glycol, propylene glycol, dipropylene glycol, neopentyl glycol, butane-1,4-diol, pentane-1,5-diol, 3-methylhexane-1,5-diol, hexane-1,6-diol, octane-1,8-diol, decane-1,10-diol, dodecane-1,12-diol, 1,12-hydroxystearyl alcohol, cyclohexane-1,4-dimethanol, dimer fatty acid diol (dimer diol), neopentyl glycol hydroxypivalate, glycerol, 1,1,1-trimethylolpropane or mixtures of the aforementioned alcohols, with organic di- or tricarboxylic acids, especially dicarboxylic acids, or the anhydrides or esters thereof, for example succinic acid, glutaric acid, adipic acid, trimethyladipic acid, suberic acid, azelaic acid, sebacic acid, dodecanedicarboxylic acid, maleic acid, fumaric acid, dimer fatty acid, phthalic acid, phthalic anhydride, isophthalic acid, terephthalic acid, dimethyl terephthalate, hexahydrophthalic acid, trimellitic acid and trimellitic anhydride, or mixtures of the aforementioned acids, and polyester polyols formed from lactones, for example from ε-caprolactone and starters such as the aforementioned di- or trihydric alcohols. Particularly suitable polyester polyols are polyester diols.

Polycarbonate polyols as obtainable by reaction, for example, of the abovementioned alcohols—used to form the polyester polyols—with dialkyl carbonates, diaryl carbonates or phosgene.

Block copolymers bearing at least two hydroxyl groups, having at least two different blocks having polyether, polyester and/or polycarbonate structure of the type described above, especially polyether polyester polyols.

Polyacrylate and polymethacrylate polyols.

Polyhydroxy-functional fats and oils, for example natural fats and oils, especially castor oil; or what are called oleochemical polyols obtained by chemical modification of natural fats and oils, for example the epoxy polyesters or epoxy polyethers obtained by epoxidation of unsaturated oils and subsequent ring opening with carboxylic acids or alcohols, or polyols obtained by hydroformylation and hydrogenation of unsaturated oils; or polyols obtained from natural fats and oils by degradation processes such as alcoholysis or ozonolysis and subsequent chemical linkage, for example by transesterification or dimerization, of the degradation products or derivatives thereof thus obtained. Suitable degradation products of natural fats and oils are especially fatty acids and fatty alcohols, and also fatty acid esters, especially the methyl esters (FAME), which can be derivatized, for example, by hydroformylation and hydrogenation to give hydroxy fatty acid esters.

Polyhydrocarbon polyols, also called oligohydrocarbonols, for example polyhydroxy-functional polyolefins, polyisobutylenes, polyisoprenes; polyhydroxy-functional ethylene-propylene, ethylene-butylene or ethylene-propylene-diene copolymers, as produced, for example, by Kraton Polymers; polyhydroxy-functional polymers of dienes, especially of 1,3 butadiene, which may also be prepared from anionic polymerization in particular; polyhydroxy-functional copolymers of dienes such as 1,3-butadiene or diene mixtures and vinyl monomers such as styrene, acrylonitrile, vinyl chloride, vinyl acetate, vinyl alcohol, isobutylene and isoprene, for example polyhydroxy-functional acrylonitrile/butadiene copolymers, as producible, for example, from epoxides or amino alcohols and carboxyl-terminated acrylonitrile/butadiene copolymers (commercially available, for example, under the Hypro® (formerly Hycar®) CTBN and CTBNX and ETBN name from Nanoresins AG, Germany, or Emerald Performance Materials LLC); and hydrogenated polyhydroxy-functional polymers or copolymers of dienes.

Preferred polyols are polyoxyalkylene polyols, polyester polyols, polycarbonate polyols and polyacrylate polyols. Particular preference is given to polyoxyalkylene polyols.

Preferred polyoxyalkylene polyols are polyoxypropylene polyols and polyoxyethylene-polyoxypropylene copolyols.

The polyol preferably has a molecular weight of 1,000 to 20,000 g/mol, more preferably of 2,000 to 20,000 g/mol.

The polyol is preferably a diol.

In addition to these polyols, it is also possible for small amounts of low molecular weight di- or polyhydric alcohols, for example ethane-1,2-diol, propane-1,2- and -1,3-diol, neopentyl glycol, diethylene glycol, triethylene glycol, the isomeric dipropylene glycols and tripropylene glycols, the isomeric butanediols, pentanediols, hexanediols, heptanediols, octanediols, nonanediols, decanediols, undecanediols, cyclohexane-1,3- and -1,4-dimethanol, hydrogenated bisphenol A, dimeric fatty alcohols, 1,1,1-trimethylolethane, 1,1,1-trimethylolpropane, glycerol, pentaerythritol, sugar alcohols such as xylitol, sorbitol or mannitol, sugars such as sucrose, other higher polyhydric alcohols, low molecular weight alkoxylation products of the aforementioned di- and polyhydric alcohols, and mixtures of the aforementioned alcohols, to be used as well in the preparation of the polyurethane polymer containing isocyanate groups.

Suitable polyisocyanates for the preparation of a polyurethane polymer containing isocyanate groups are especially the following commercially available polyisocyanates or any desired mixtures thereof:

aliphatic isocyanates such as, in particular, tetramethylene 1,4-diisocyanate, 2-methylpentamethylene 1,5-diisocyanate, hexamethylene 1,6-diisocyanate (HDI), 2,2,4- and 2,4,4-trimethylhexamethylene 1,6-diisocyanate (TMDI), decamethylene 1,10-diisocyanate, dodecamethylene 1,12-diisocyanate, lysine and lysine ester diisocyanate, cyclohexane 1,3- and 1,4-diisocyanate, 1-methyl-2,4- and -2,6-diisocyanatocyclohexane and any desired mixtures of these isomers (HTDI or $H_6$TDI), 1-isocyanato-3,3,5-trimethyl-5-isocyanatomethylcyclohexane (=isophorone diisocyanate or IPDI), perhydro-2,4'- and -4,4'-diphenylmethane diisocyanate (HMDI or $H_{12}$MDI), 1,4-diisocyanato-2,2,6-trimethylcyclohexane (TMCDI), 1,3- and 1,4-bis-(isocyanatomethyl)cyclohexane, m- and p-xylylene diisocyanate (m- and p-XDI), tetramethyl-1,3- and -1,4-xylylene diisocyanate (m- and p-TMXDI), bis-(1-isocyanato-1-methylethyl)naphthalene, dimer and trimer fatty acid isocyanates such as 3,6-bis-(9-isocyanatononyl)-4,5-di-(1-heptenyl)cyclohexene (dimeryl diisocyanate) and α,α,α',α',α'',α''-hexamethylmesitylene 1,3,5-triisocyanat, and additionally aromatic isocyanates such as, in particular tolylene 2,4- and 2,6-diisocyanate and any desired mixtures of these isomers (TDI), diphenylmethane 4,4'-, 2,4'- and 2,2'-diisocyanate and any desired mixtures of these isomers (MDI), mixtures of MDI and MDI homologs (polymeric MDI or PMDI), phenylene 1,3- and 1,4-diisocyanate, 2,3,5,6-tetramethyl-1,4-diisocyanatobenzene, naphthalene 1,5-diisocyanate (NDI), 3,3'-dimethyl-4,4'-diisocyanatodiphenyl (TODI), dianisidine diisocyanate (DADI), 1,3,5-tris(isocyanatomethyl)benzene, tris(4-isocyanatophenyl)methane and tris(4-isocyanatophenyl) thiophosphate, and oligomers and polymers of the aforementioned isocyanates, and any desired mixtures of the aforementioned isocyanates.

Preferred polyisocyanates are diisocyanates. Particular preference is given to IPDI, HDI, MDI and TDI, especially IPDI. On the basis of IPDI, it is possible to obtain polymers having end groups of the formula (VI) bonded to cycloaliphatic radicals. Polymers of this kind enable compositions having particularly good light stability and stability to discoloration.

A further means of preparing a polymer having end groups of the formula (VI) is to react the hydroxysilane of the formula (I) with a polyisocyanate in such a way that an isocyanatosilane containing urethane groups is formed, which is in turn converted by approximately stoichiometric reaction with a suitable polyol to the polymer having end groups of the formula (VI). It is advantageous here to use the polyisocyanates and polyols mentioned as preferred for preparation of a polymer having isocyanate groups.

The polymer having end groups of the formula (VI) is very storage-stable under exclusion of moisture. On contact with moisture, the end groups of the formula (VI) are hydrolyzed, whereupon the polymer cures to form a crosslinked plastic. The present invention thus also relates to a crosslinked plastic which is obtained by the reaction of at least one polymer having end groups of the formula (VI) with moisture.

The polymer having end groups of the formula (VI) has advantageous properties. Its viscosity is comparatively low, which is advantageous for the further processing thereof, for example as a moisture-curing composition. It has excellent storage stability and cures rapidly with moisture to give an elastic material having good strength and extensibility and good thermal stability.

The polymer having end groups of the formula (VI) is especially usable as a constituent of a curable composition, especially as a constituent of a moisture-curing composition.

Such a moisture-curing composition contains the at least one polymer having end groups of the formula (VI) and at least one further constituent.

Preferably, the moisture-curing composition has a content of polymer having end groups of the formula (VI) of 5% to 90% by weight, especially 10% to 60% by weight.

Suitable further constituents are especially catalysts, crosslinkers, plasticizers, fillers, pigments, solvents, adhesion promoters, desiccants, rheology assistants, flame retardants and stabilizers.

Preferably, the moisture-curing composition comprises at least one catalyst which accelerates the crosslinking of polymers containing silane groups. Suitable catalysts for the purpose are especially metal catalysts and/or nitrogen compounds.

Suitable metal catalysts are compounds of titanium, zirconium, aluminum and tin, especially organotin compounds, organotitanates, organozirconates and organoaluminates, where these metal catalysts especially have alkoxy groups, aminoalkoxy groups, sulfonate groups, carboxyl groups, 1,3-diketonate groups, 1,3-ketoesterate groups, dialkylphosphate groups and dialkylpyrophosphate groups.

Particularly suitable organotin compounds are dialkyltin oxides, dialkyltin dichlorides, dialkyltin dicarboxylates and dialkyltin diketonates, especially dibutyltin oxide, dibutyltin dichloride, dibutyltin diacetate, dibutyltin dilaurate, dibutyltin diacetylacetonate, dioctyltin oxide, dioctyltin dichloride, dioctyltin diacetate, dioctyltin dilaurate and dioctyltin diacetylacetonate, and also alkyltin thioesters.

Particularly suitable organotitanates are as follows:
titanium(IV) complexes having two 1,3-diketonate ligands, especially 2,4-pentanedionate (=acetylacetonate), and two alkoxide ligands;
titanium(IV) complexes having two 1,3-ketoesterate ligands, especially ethylacetoacetate, and two alkoxide ligands;
titanium(IV) complexes having one or more aminoalkoxide ligands, especially triethanolamine or 2-((2-aminoethyl)amino)ethanol, and one or more alkoxide ligands;
titanium(IV) complexes having four alkoxide ligands;
and more highly condensed organotitanates, especially oligomeric titanium(IV) tetrabutoxide, also referred to as polybutyl titanate;
where suitable alkoxide ligands are especially isobutoxy, n-butoxy, isopropoxy, ethoxy and 2-ethylhexoxy.

Very particularly suitable organotitanates are bis(ethylacetoacetato)-diisobutoxytitanium(IV), bis(ethylacetoacetato) diisopropoxytitanium(IV), bis(acetylacetonato)diisopropoxytitanium(IV), bis(acetylacetonato)diisobutoxytitanium(IV), tris(oxyethyl)amineisopropoxytitanium(IV), bis[tris(oxyethyl)-amine]diisopropoxytitanium(IV), bis(2-ethylhexane-1,3-dioxy)titanium(IV), tris[2-((2-aminoethyl) amino)ethoxy]ethoxytitanium(IV), bis(neopentyl(diallyl) oxy-diethoxytitanium(IV), titanium(IV) tetrabutoxide, tetra (2-ethylhexyloxy)titanate, tetra(isopropoxy)titanate and polybutyl titanate.

Especially suitable are the following commercially available products: Tyzor® AA, GBA, GBO, AA-75, AA-65, AA-105, DC, BEAT, BTP, TE, TnBT, KTM, TOT, TPT or IBAY (all from Du Pont/Dorf Ketal); Tytan PBT, TET, X85, TAA, ET, S2, S4 or S6 (all from TensoChema) and Ken-React® KR® TTS, 7, 9QS, 12, 26S, 33DS, 38S, 39DS, 44, 134S, 138S, 133DS, 158FS or LICA® 44 (all from Kenrich Petrochemicals).

Particularly suitable organozirconates are the following commercially available products: Ken-React® NZ® 38J, KZ® TPPJ, KZ® TPP, NZ® 01, 09, 12 38, 44 or 97 (all from Kenrich Petrochemicals) and Snapcure® 3020, 3030, 1020 (all from Johnson Matthey & Brandenberger).

A particularly suitable organoaluminate is the commercially available product K-Kat 5218 (from King Industries).

Particularly suitable metal catalysts are additionally titanates, zirconates and aluminates having sulfonate or phosphate or pyrophosphate ligands. Particularly suitable titanates having sulfonate, phosphate or pyrophosphate ligands are the following commercially available products: Ken-React® LICA® 09, LICA® 12, KR® 212, LICA® 38, LICA® 38J, KR® 238S, KR® 262ES and KR® 262ES (all from Kenrich Petrochemicals).

Particularly suitable zirconates having sulfonate, phosphate or pyrophosphate ligands are the following commercially available products: Ken-React® NZ® 09, NZ® 12 and NZ® 38 (all from Kenrich Petrochemicals).

A particularly suitable aluminate having a phosphate ligand is the commercially available Ken-React® KA® 489 A (from Kenrich Petrochemicals).

Nitrogen compounds suitable as catalyst are especially amines such as, in particular, N-ethyldiisopropylamine, N,N,N',N'-tetramethylalkylenediamines, polyoxyalkyleneamines, 1,4-diazabicyclo[2.2.2]octane; aminosilanes such as, in particular, 3-aminopropyltrimethoxysilane, 3-aminopropyldimethoxymethyl-silane, N-(2-aminoethyl)-3-aminopropyltrimethoxysilane, N-(2-aminoethyl)-3-aminopropylmethyldimethoxysilane, N-(2-aminoethyl)-N'-[3-(trimethoxysilyl)-propyl]ethylenediamine and the analogs thereof having ethoxy or isopropoxy in place of the methoxy groups on the silicon; amidines such as, in particular, 1,8-diazabicyclo[5.4.0]undec-7-ene (DBU), 1,5-diazabicyclo[4.3.0]non-5-ene (DBN), 6-dibutylamino-1,8-diazabicyclo[5.4.0]undec-7-ene; guanidines such as, in particular, tetramethylguanidine, 2-guanidinobenzimidazole, acetylacetoneguanidine, 1,3-di-o-tolylguanidine, 2-tert-butyl-1,1,3, 3-tetramethylguanidine; and imidazoles such as, in particular, N-(3-trimethoxy-silylpropyl)-4,5-dihydroimidazole and N-(3-triethoxysilylpropyl)-4,5-dihydroimidazole.

Also especially suitable are combinations of various catalysts, especially combinations of at least one metal catalyst and at least one nitrogen compound.

Preferred catalysts are organotin compounds, organotitanates, amines, amidines, guanidines and imidazoles. Particular preference is given to organotitanates and amidines.

Further suitable constituents of the moisture-curing composition are especially the following auxiliaries and additives:
adhesion promoters and/or crosslinkers, especially silanes such as the aminosilanes already mentioned as catalyst, aminosilanes having secondary amino groups, such as, in particular, N-phenyl-, N-cyclohexyl- and N-alkylaminosilanes, and additionally mercaptosilanes, epoxysilanes, (meth)acryloylsilanes, anhydridosilanes, carbamatosilanes, alkylsilanes and iminosilanes, and oligomeric forms of these silanes, and adducts formed from primary aminosilanes with epoxysilanes or (meth)acryloylsilanes or anhydridosilanes. Especially suitable are 3-glycidoxypropyltrimethoxysilane, 3-aminopropyltrimethoxysilane, N-(2-aminoethyl)-3-aminopropyltrimethoxysilane, N-(2-aminoethyl)-N'-[3-(trimethoxysilyl)propyl]ethylenediamine, 3-mercaptopropyltrimethoxysilane, 3-ureidopropyltrimethoxysilane and the corresponding silanes having ethoxy groups in place of the methoxy groups, and oligomeric forms of these silanes;

plasticizers, especially carboxylic esters such as phthalates, especially dioctyl phthalate, diisononyl phthalate or diisodecyl phthalate, hydrogenated phthalates, adipates, especially dioctyl adipate, azelates, sebacates, polyols, especially polyoxyalkylenepolyols or polyesterpolyols, glycol ethers, glycol esters, organic phosphoric and sulfonic esters or polybutenes;

solvents;

inorganic and organic fillers, especially natural, ground or precipitated calcium carbonates optionally coated with fatty acids, especially stearic acid, baryte (heavy spar), talcs, quartz flours, quartz sand, dolomites, wollastonites, kaolins, calcined kaolins, mica (potassium aluminum silicate), molecular sieves, aluminum oxides, aluminum hydroxides, magnesium hydroxide, silicas including finely divided silicas from pyrolysis processes, industrially produced carbon blacks, graphite, metal powders such as aluminum, copper, iron, silver or steel, PVC powder or hollow beads;

fibers, especially glass fibers, carbon fibers, metal fibers, ceramic fibers or polymer fibers such as polyamide fibers or polyethylene fibers;

dyes;

pigments, especially titanium dioxide or iron oxides;

desiccants, especially tetraethoxysilane, vinyltrimethoxy- or vinyltriethoxysilane and organoalkoxysilanes having a functional group in the $\alpha$ position to the silane group, especially N-(methyldimethoxysilylmethyl)-O-methylcarbamate, (methacryloyloxymethyl)silanes, methoxymethylsilanes, orthoformic esters, and also calcium oxide or molecular sieves;

rheology assistants, especially thickeners, especially sheet silicates such as bentonites, derivatives of castor oil, hydrogenated castor oil, polyamides, polyurethanes, urea compounds, fumed silicas, cellulose ethers and hydrophobically modified polyoxyethylenes;

stabilizers against oxidation, heat, light and UV radiation;

natural resins, fats or oils such as rosin, shellac, linseed oil, castor oil and soya oil;

nonreactive polymers such as, in particular, homo- or copolymers of unsaturated monomers, especially from the group comprising ethylene, propylene, butylene, isobutylene, isoprene, vinyl acetate and alkyl(meth)acrylates, especially polyethylenes (PE), polypropylenes (PP), polyisobutylenes, ethylene-vinyl acetate copolymers (EVA) and atactic poly-$\alpha$-olefins (APAO);

flame-retardant substances, especially the aluminum hydroxide and magnesium hydroxide fillers already mentioned, and also especially organic phosphoric esters such as, in particular, triethyl phosphate, tricresyl phosphate, triphenyl phosphate, diphenyl cresyl phosphate, isodecyl diphenyl phosphate, tris(1,3-dichloro-2-propyl)phosphate, tris(2-chloroethyl)phosphate, tris (2-ethylhexyl)phosphate, tris(chloroisopropyl) phosphate, tris(chloropropyl)phosphate, isopropylated triphenyl phosphate, mono-, bis- and tris(isopropylphenyl)phosphate of different isopropylation levels, resorcinol bis(diphenyl phosphate), bisphenol A bis(diphenyl phosphate) and ammonium polyphosphates;

surface-active substances, especially wetting agents, leveling agents, deaerators or defoamers;

biocides, especially algicides, fungicides or substances that inhibit fungal growth;

and further substances customarily used in moisture-curing compositions.

It may be advisable to chemically or physically dry certain constituents before mixing them into the moisture-curing composition.

The moisture-curing composition may, as well as the polymer having end groups of the formula (VI), comprise further oligo- or polymers containing silane groups.

In a preferred embodiment, the moisture-curing composition is free of organotin compounds. This may be advantageous for environmental and/or toxicological reasons.

In a further preferred embodiment, the moisture-curing composition does not release any methanol in the course of curing thereof. This may be advantageous for environmental and/or toxicological reasons.

The moisture-curing composition is preferably produced and kept with exclusion of moisture. Typically, the composition is storage-stable, meaning that it can be kept with exclusion of moisture in a suitable package or arrangement such as, in particular, a drum, pouch or cartridge, over a period of several months up to one year or longer, without any change in its use properties or in its properties after curing to a degree of relevance for use thereof. Typically, the storage stability is determined by the measurement of viscosity or expression force.

The moisture-curing composition may take the form of a one-pack composition or of a two-pack composition.

A "one-pack" composition in the present document refers to a curable composition in which all the constituents of the composition are stored in a mixture in the same container, and which is storage-stable at room temperature over a period of several weeks to months and is curable with moisture.

A "two-pack" composition in the present document refers to a composition in which the constituents of the composition are present in two separate packs which are stored in separate containers and which are each storage-stable per se at room temperature. Only shortly before or during the application of the composition are the two packs mixed with one another, whereupon the mixed composition cures, the curing proceeding or being completed only through the action of moisture.

When the moisture-curing composition is applied to at least one solid body or article, the silane groups present come into contact with moisture. The silane groups have the property of being hydrolyzed on contact with moisture. This forms organosilanols and, via subsequent condensation reactions, organosiloxanes. As a result of these reactions, the composition ultimately cures. This process is also referred to as crosslinking. In addition, silanol groups can condense with hydroxyl groups, for example, in the substrate to which the composition has been applied, which can result in formation of excellent adhesion of the composition on the substrate in the course of curing. The water required for the curing may either come from the air (air humidity), or the composition can be contacted with a water-containing component, for example by spreading, for example with a smoothing agent, or by spraying, or it is possible to add a water-containing component to the composition in the course of application, for example in the form of an aqueous paste which is mixed in, for example, by means of a static mixer.

According to the temperature, nature of contact, amount of moisture and presence of any catalysts, the curing proceeds at different speed. In the case of curing by means of air humidity, a skin is at first formed at the surface of the composition. What is called the skinning time is accordingly a measure of the curing rate.

In the cured state, the composition has elastic properties, especially a good strength and high extensibility, good thermal stability and good adhesion properties on various substrates. As a result, it is suitable for a multitude of uses, especially as a fiber composite, potting compound, sealant, adhesive, covering, coating or paint for construction and industrial applications, for example as an electrical insulation compound, spackling compound, joint sealant, assembly adhesive, bodywork adhesive, glazing adhesive, sandwich element adhesive, laminating adhesive, laminate adhesive, anchoring adhesive, wall covering and coating, balcony and roof coating, concrete protection coating, parking garage coating and anticorrosion paint, as seal, paint, varnish and primer.

The moisture-curing composition is particularly suitable as a sealant and/or adhesive, especially for joint sealing and for elastic adhesive bonds in construction and industrial applications.

For use of the composition as a sealant, for example for joints in construction or civil engineering, or for use as an adhesive for elastic adhesive bonds, for example in motor vehicle construction, the composition preferably has a pasty consistency with properties of structural viscosity. Such a pasty sealant or adhesive is applied to the substrate by means of a suitable device. Suitable methods for application are, for example, application from commercial cartridges, which are operated manually or by means of compressed air, or from a drum or pail by means of a conveying pump or an extruder, optionally by means of an application robot.

A sealant or adhesive having good application properties has high sag resistance and forms short threads. This means that it remains stationary in the form applied, i.e. does not flow away after application, and forms only a very short thread, if any, after the application device has been moved away, and so the substrate does not become soiled.

An adhesive for elastic bonds, for example in motor vehicle construction, is preferably applied in the form of a bead having an essentially round or triangular cross-sectional area.

In the application as an adhesive, the composition is applied to a substrate S1 and/or a substrate S2. The adhesive can thus be applied to one or the other substrate or to both substrates. Thereafter, the parts to be bonded are joined, whereupon the adhesive cures through contact with moisture. It should be ensured here that the parts are joined within what is called the open time, in order to make sure that the two joint parts are reliably bonded to one another. In the application as a sealant, the composition is applied between the substrates S1 and S2 and then the composition is cured by contact with moisture. Typically, the sealant is injected into a joint.

In both applications, the substrate S1 may be the same as or different than substrate S2.

Suitable substrates S1 or S2 are especially
glass, glass ceramic, concrete, mortar, brick, tile, gypsum and natural rocks such as granite or marble;
metals and alloys such as aluminum, iron, steel and nonferrous metals, and also surface-finished metals and alloys such as galvanized or chromed metals;
leather, textiles, paper, wood, woodbase materials bonded with resins, for example phenolic, melamine or epoxy resins, resin-textile composites and further polymer composites;
plastics such as polyvinyl chloride (rigid and flexible PVC), acrylonitrile-butadiene-styrene copolymers (ABS), polycarbonate (PC), polyamide (PA), polyesters, poly(methylmethacrylate) (PMMA), polyesters, epoxy resins, polyurethanes (PUR), polyoxymethylene (POM), polyolefins (PO), polyethylene (PE) or polypropylene (PP), ethylene/propylene copolymers (EPM) and ethylene/propylene/diene terpolymers (EPDM), where the plastics may preferably have been surface-treated by means of plasma, corona or flames;
fiber-reinforced plastics such as carbon fiber-reinforced plastics (CFP), glass fiber-reinforced plastics (GFP) and sheet molding compounds (SMC);
coated substrates such as powder-coated metals or alloys;
paints and lacquers, especially automotive topcoats.

The substrates may be pretreated if required prior to the application of the adhesive or sealant. Pretreatments of this kind especially include physical and/or chemical cleaning methods, for example grinding, sandblasting, brushing or the like, or treating with detergents or solvents or the application of an adhesion promoter, an adhesion promoter solution or a primer.

After the substrates S1 and S2 have been bonded or sealed by means of an inventive composition, a bonded or sealed article is obtained. Such an article may be a built structure, especially a built structure in construction or civil engineering, or it may be a means of transport, for example a land or water vehicle, especially an automobile, a bus, a truck, a train or a ship, or an installable component thereof.

EXAMPLES

Detailed hereinafter are working examples which are intended to illustrate the invention described in detail. It will be appreciated that the invention is not restricted to these described working examples.

"Standard climatic conditions" are understood to mean a temperature of 23±1° C. and a relative air humidity of 50±5%. "SCC" stands for standard climatic conditions.

1. Preparation of Hydroxysilanes

Hydroxysilane HS-1: 2-morpholino-4(5)-(2-trimethoxysilylethyl)cyclohexan-1-ol

In a round-bottom flask, 32.85 g (133.33 mmol) of β-(3,4-epoxycyclohexyl)-ethyltrimethoxysilane (Silquest® A-186 from Momentive), 15.34 g (176.08 mmol) of anhydrous morpholine and 0.10 g of lanthanum(III) triflate were stirred at 110° C. under a nitrogen atmosphere over the course of 2 h until no further reaction progress was found by means of gas chromatography. The crude product was aftertreated at 80° C. and about 1 mbar over the course of 30 minutes. A liquid product having a theoretical OH equivalent weight of 333.5 g was obtained.

After the preparation, the product had a purity of 98% to 99% by weight (determined by means of gas chromatography). After storage with exclusion of moisture at room temperature for 3 months, the purity was unchanged.

Hydroxysilane HS-2: 2-Pyrrolidino-4(5)-(2-trimethoxysilylethyl)cyclohexan-1-ol As described for the hydroxysilane HS-1, 32.85 of Silquest® A-186, 12.54 g of pyrrolidine and 0.10 g of lanthanum(III) triflate were converted. A liquid product having a theoretical OH equivalent weight of 317.5 g was obtained, which had not undergone any noticeable change after a storage time of 3 months at room temperature.

Hydroxysilane HS-3: 2-dibutylamino-4(5)-(2-trimethoxysilylethyl)cyclohexan-1-ol As described for the hydroxysilane HS-1, 32.85 g of Silquest® A-186, 22.76 g of dibutylamine and 0.10 g of lanthanum(III) triflate were converted. A liquid product having a theoretical OH equivalent weight of 375.6 g was obtained, which had not undergone any noticeable change after a storage time of 3 months at room temperature.

Hydroxysilane HS-4: 2-morpholino-4(5)-(2-triethoxysilylethyl)cyclohexan-1-ol In a round-bottom flask, 38.46 g (133.33 mmol) of β-(3,4-epoxycyclohexyl)-ethyltriethoxysilane (CoatOSil® 1770 from Momentive), 15.34 g (176.08 mmol) of anhydrous morpholine and 0.10 g of lanthanum(III) triflate were stirred under a nitrogen atmosphere at 110° C. over the course of 2 h until no further reaction progress was found by means of gas chromatography. The crude product was aftertreated at 80° C. and about 1 mbar over the course of 30 minutes. A liquid product having a theoretical OH equivalent weight of 375.6 g was obtained. After the preparation, the product had a purity of 97% to 98% by weight (determined by means of gas chromatography). After storage with exclusion of moisture at room temperature for 3 months, the purity was unchanged.

Hydroxysilane HS-5: 2-pyrrolidino-4(5)-(2-triethoxysilylethyl)cyclohexan-1-ol As described for the hydroxysilane HS-4, 38.46 g of CoatOSil® 1770, 12.54 g of pyrrolidine and 0.10 g of lanthanum(III) triflate were converted. A liquid product having a theoretical OH equivalent weight of 359.6 g was obtained, which had not undergone any noticeable change after a storage time of 3 months at room temperature.

Hydroxysilane HS-6: 2-(4-methylpiperazino)-4(5)-(2-triethoxysilylethyl)-cyclohexan-1-ol As described for the hydroxysilane HS-4, 38.46 g of CoatOSil® 1770, 17.64 g of 4-methylpiperazine and 0.10 g of lanthanum(III) triflate were converted. A liquid product having a theoretical OH equivalent weight of 388.6 g was obtained, which had not undergone any noticeable change after a storage time of 3 months at room temperature.

Hydroxysilane HS-7: 2-dibutylamino-4(5)-(2-triethoxysilylethyl)cyclohexan-1-ol As described for the hydroxysilane HS-4, 38.46 g of CoatOSil® 1770, 22.76 g of dibutylamine and 0.10 g of lanthanum(III) triflate were converted. A liquid product having a theoretical OH equivalent weight of 417.7 g was obtained, which had not undergone any noticeable change after a storage time of 3 months at room temperature.

Hydroxysilane HS-R1: 1-Morpholino-3-(3-trimethoxysilylpropoxy)propan-2-ol

In a round-bottom flask, 28.36 g (120 mmol) of 3-glycidoxypropyltrimethoxysilane (Dynasylan® GLYMO from Evonik Degussa), 12.55 g (144.1 mmol) of anhydrous morpholine and 7.00 g of anhydrous methanol were stirred under a nitrogen atmosphere and under reflux at 80° C. over the course of 5 h until no further reaction progress was found by means of gas chromatography. The crude product was aftertreated at 80° C. and about 1 mbar over the course of 30 minutes. A liquid product having a theoretical OH equivalent weight of 323.5 g was obtained.

The reaction product had a purity of 76% by weight after the preparation and a purity of 52% by weight after storage with exclusion of moisture at room temperature for 1 month (determined by means of gas chromatography).

Hydroxysilane HS-R2: 1-morpholino-3-(3-triethoxysilylpropoxy)propan-2-ol

As described for the hydroxysilane HS-R1, 33.41 g (120 mmol) of 3-glycidoxy-propyltriethoxysilane (Dynasylan® GLYEO from Evonik Degussa), 12.55 g of anhydrous morpholine and 7.00 g of anhydrous ethanol were converted. A liquid product having a theoretical OH equivalent weight of 365.5 g was obtained.

The reaction product had a purity of 94% by weight after the preparation and a purity of 83% by weight after storage with exclusion of moisture at room temperature for 1 month (determined by means of gas chromatography).

The hydroxysilanes HS-1 to HS-7 are inventive hydroxysilanes of the formula (I); the hydroxysilanes HS-R1 and HS-R2 are noninventive hydroxysilanes for comparative purposes.

A comparison of the purity of the hydroxysilanes prepared and stored shows that the inventive hydroxysilanes HS-1 (trimethoxysilane) and HS-4 (triethoxysilane) had a very high purity and excellent storage stability, while the comparative hydroxysilane HS-R1 (trimethoxysilane) was neither preparable in satisfactory purity nor storage-stable, and the comparative hydroxysilane HS-R2 (triethoxysilane) did have satisfactory purity after preparation but was not storage-stable.

2. Preparation of Polymers Containing Silane Groups
Polymers SP-1 to SP-7

For each polymer, 100 parts by weight (PW) of polymer 1 were mixed with the hydroxysilane specified in table 1 in the amount specified (OH/NCO=1.10). This mixture was stirred at 90° C. under a nitrogen atmosphere until no isocyanate groups were detectable any longer by means of IR spectroscopy (about 2 hours). Subsequently, the reaction mixture was cooled and kept with exclusion of moisture.

The viscosity was determined the day after the preparation in each case in a thermostated Rheotec RC30 cone-plate viscometer (cone diameter 50 mm, cone angle 1°, cone tip-plate distance 0.05 mm, shear rate 10 s$^{-1}$) at a temperature of 20° C.

The properties of the polymers containing silane groups obtained are reported in table 1.

The polymers SP-1 to SP-7 are inventive polymers having end groups of the formula (VI).

Polymer 1 was prepared by mixing 720 g of Acclaim® 12200 polyol (Bayer Material Science; low monool polyoxypropylene diol; OH number 11.0 mg KOH/g; water content of about 0.02% by weight), 34.5 g of isophorone diisocyanate (Vestanat® IPDI, Evonik Degussa), 80.0 g of diisodecyl phthalate and 0.2 g of dibutyltin dilaurate under a nitrogen atmosphere, heated to 90° C. with constant stirring and left at this temperature until the content of free isocyanate groups determined by titrimetric means reached a value of 0.73% by weight. The product was cooled to room temperature and kept with exclusion of moisture.

time until, when the surface of the composition was tapped gently by means of an LDPE pipette, there were no remaining residues on the pipette for the first time was determined.

To determine the mechanical properties, the composition was cast on a PTFE-coated film to give a film of thickness 2 mm, which was stored under standard climatic conditions for 2 weeks, some dumbbells having a length of 75 mm with a bar length of 30 mm and a bar width of 4 mm were punched out of the film and these were tested in accordance with DIN EN 53504 at a pulling speed of 200 mm/min for tensile strength (breaking force), elongation at break and modulus of elasticity (modulus of elasticity at 0.5%-50% elongation). Shore A hardness was determined in accordance with DIN 53505 on test specimens which had been cured under standard climatic conditions for 14 days.

TABLE 1

Composition and properties of the polymers SP-1 to SP-7 containing silane groups.

| Polymer | SP-1 | SP-2 | SP-3 | SP-4 | SP-5 | SP-6 | SP-7 |
|---|---|---|---|---|---|---|---|
| Polymer 1 | 100.00 | 100.00 | 100.00 | 100.00 | 100.00 | 100.00 | 100.00 |
| Hydroxysilane | HS-1, 6.38 | HS-2, 6.07 | HS-3, 7.18 | HS-4, 7.18 | HS-5, 6.88 | HS-6, 7.43 | HS-7, 7.99 |
| Viscosity [Pa · s] | 80 | 136 | 118 | 66 | 130 | 83 | 138 |

3. Production of Moisture-Curing Compositions

Compositions Z-1 to Z-7

For each composition, the ingredients specified in table 2 were mixed in the amounts specified (in parts by weight) by means of a centrifugal mixer (SpeedMixer™ DAC 150, FlackTek Inc.) with exclusion of moisture and kept. Each composition was tested as follows:

To determine the skinning time, a few grams of the composition were applied to cardboard in a layer thickness of about 2 mm and, under standard climatic conditions, the These results are appended with "SCC:".

As a measure of thermal stability, some dumbbells and the Shore A test specimens after the 2 weeks under standard climatic conditions were additionally stored in an air circulation oven at 90° C. for 1 week and then tested in the same way for tensile strength, elongation at break and modulus of elasticity, or for Shore A hardness. These results are appended with "90° C.:". The results are reported in table 2.

TABLE 2

Composition and properties of the compositions Z-1 to Z-7.

| Composition | Z-1 | Z-2 | Z-3 | Z-4 | Z-5 | Z-6 | Z-7 |
|---|---|---|---|---|---|---|---|
| Polymer | SP-1, 82.5 | SP-2, 82.5 | SP-3, 82.5 | SP-4, 82.5 | SP-5, 82.5 | SP-6, 82.5 | SP-7, 82.5 |
| Silquest ® A-1120 [1] | 3.8 | 3.8 | 3.8 | — | — | — | — |
| Geniosil ® GF-94 [2] | — | — | — | 3.2 | 3.2 | 3.2 | 3.2 |
| Silquest ® A-171 [3] | 0.3 | 0.3 | 0.3 | — | — | — | — |
| Dynasilan ® VTEO [4] | — | — | — | 0.3 | 0.3 | 0.3 | 0.3 |
| DBTDL (10%) [5] | 0.4 | 0.4 | 0.4 | — | — | — | — |
| DBTDL (50%) [6] | — | — | — | 1.0 | 1.0 | 1.0 | 1.0 |
| Diisodecyl phthalate | 13.0 | 13.0 | 13.0 | 13.0 | 13.0 | 13.0 | 13.0 |
| Skinning time [min] | 75 | 20 | 30 | 420 | 160 | 210 | 200 |
| SCC: Shore A | 33 | 22 | 24 | 34 | 31 | 24 | 22 |
| Tensile strength [MPa] | 0.58 | 0.37 | 0.42 | 0.35 | 0.55 | 0.53 | 0.43 |
| Elongation at break [%] | 102 | 103 | 113 | 92 | 90 | 95 | 100 |
| Modulus of elasticity [MPa] | 0.65 | 0.34 | 0.38 | 0.24 | 0.62 | 0.57 | 0.42 |
| 90° C.: Shore A | 36 | 21 | 24 | 33 | 33 | 32 | 28 |
| Tensile strength [MPa] | 0.60 | 0.36 | 0.41 | 0.55 | 0.52 | 0.47 | 0.36 |
| Elongation at break [%] | 91 | 102 | 112 | 83 | 81 | 80 | 66 |
| Modulus of elasticity [MPa] | 0.66 | 0.32 | 0.36 | 0.68 | 0.62 | 0.57 | 0.47 |

[1] N-(2-Aminoethyl)-3-aminopropyltrimethoxysilane from Momentive
[2] N-(2-Aminoethyl)-3-aminopropyltriethoxysilane from Wacker
[3] Vinyltrimethoxysilane from Momentive
[4] Vinyltriethoxysilane from Evonik
[5] Dibutyltin dilaurate 10% by weight in diisodecyl phthalate
[6] Dibutyltin dilaurate 50% by weight in diisodecyl phthalate Compositions Z-8 to Z-14

For each composition, the ingredients specified in table 3 were processed in the amounts specified (in parts by weight) in a vacuum mixer at 50° C. with exclusion of moisture over the course of 30 minutes to give a homogeneous paste and kept. Each composition was tested as follows:
skinning time, tensile strength, elongation at break, moduli of elasticity and Shore A hardness were determined as described for composition Z-1. For the heated storage, however, the dumbbells, after the 2 weeks under standard climatic conditions, were stored at 100° C. for 4 weeks. These results are appended with "100° C.:".

The results are reported in table 3.

The thixotropic paste was produced by initially charging a vacuum mixer with 300 g of diisodecyl phthalate (Palatinol® Z, BASF) and 48 g of 4,4'-methylene-diphenyl diisocyanate (Desmodur® 44 MC L, Bayer), gently heating them and then gradually adding 27 g of monobutylamine dropwise while stirring vigorously. Stirring of the paste formed was continued under reduced pressure while cooling for one hour.

$$----R^3-\underset{\underset{(OR^5)_{3-x}}{|}}{\overset{(R^4)_x}{|}}Si \quad (II)$$

$R^1$ and $R^2$ are either each individually an alkyl radical having 1 to 12 carbon atoms and optionally having heteroatoms in the form of ether oxygen, thioether sulfur or tertiary amine nitrogen, or together are an alkylene radical having 2 to 12 carbon atoms and optionally having heteroatoms in the form of ether oxygen, thioether sulfur or tertiary amine nitrogen;

$R^3$ is a linear or branched alkylene or cycloalkylene radical having 1 to 20 carbon atoms, optionally having aromatic moieties, and optionally having one or more heteroatoms;

$R^4$ is an alkyl group having 1 to 8 carbon atoms;

$R^5$ is an alkyl group having 1 to 10 carbon atoms and optionally having one or more ether oxygen heteroatoms; and x is 0 or 1 or 2.

TABLE 3

Composition and properties of the compositions Z-8 to Z-14.

| Composition | Z-8 | Z-9 | Z-10 | Z-11 | Z-12 | Z-13 | Z-14 |
| --- | --- | --- | --- | --- | --- | --- | --- |
| Polymer | SP-1, | SP-2, | SP-3, | SP-4, | SP-5, | SP-6 | SP-7, |
|  | 15.00 | 15.00 | 15.00 | 15.00 | 15.00 | 15.00 | 15.00 |
| Diisodecyl phthalate | 20.00 | 20.00 | 20.00 | 20.00 | 20.00 | 20.00 | 20.00 |
| Thixotropic paste | 2.00 | 2.00 | 2.00 | 2.00 | 2.00 | 2.00 | 2.00 |
| Silquest ® A-171 [1] | 1.00 | 1.00 | 1.00 | — | — | — | — |
| Dynasilan ® VTEO [2] | — | — | — | 1.00 | 1.00 | 1.00 | 1.00 |
| Socal ® U 1 S2 [3] | 10.00 | 10.00 | 10.00 | 10.00 | 10.00 | 10.00 | 10.00 |
| Omyacarb ® 5 GU [4] | 50.00 | 50.00 | 50.00 | 50.00 | 50.00 | 50.00 | 50.00 |
| Dynasylan ® AMMO [5] | 0.75 | 0.75 | 0.75 | — | — | — | — |
| Dynasylan ® AMEO [6] | — | — | — | 0.75 | 0.75 | 0.75 | 0.75 |
| DBTDL (10%) [7] | 1.00 | 1.00 | 1.00 | — | — | — | — |
| Polycat ® DBU [8] | — | — | — | 0.20 | 0.20 | 0.20 | 0.20 |
| Tyzor ® IBAY [9] | — | — | — | 1.00 | 1.00 | 1.00 | 1.00 |
| Skinning time [min] | 25 | 10 | 5 | 270 | 185 | 55 | 80 |
| SCC: Shore A | 41 | 32 | 27 | 32 | 29 | 31 | 23 |
| Tensile strength [MPa] | 1.50 | 1.08 | 1.06 | 1.07 | 0.92 | 0.90 | 0.84 |
| Elongation at break [%] | 136 | 132 | 178 | 527 | 529 | 555 | 676 |
| Modulus of elasticity [MPa] | 1.20 | 0.77 | 0.65 | 0.75 | 0.61 | 0.58 | 0.38 |
| 100° C.: Shore A | 27 | 18 | 11 | 34 | 32 | 37 | 29 |
| Tensile strength [MPa] | 0.87 | 0.55 | 0.41 | 0.88 | 0.81 | 1.02 | 0.80 |
| Elongation at break [%] | 85 | 83 | 79 | 100 | 85 | 121 | 134 |
| Modulus of elasticity [MPa] | 0.94 | 0.64 | 0.48 | 1.01 | 1.07 | 1.11 | 0.79 |

[1] Vinyltrimethoxysilane from Momentive
[2] Vinyltriethoxysilane from Evonik
[3] Precipitated coated calcium carbonate from Solvay
[4] Calcium carbonate from Omya
[5] 3-Aminopropyltrimethoxysilane from Evonik
[6] 3-Aminopropyltriethoxysilane from Evonik
[7] Dibutyilin dilaurate 10% by weight in diisodecyl phthalate
[8] 1,8-Diazabicyclo[5.4.0]undec-7-ene from Air Products
[9] Titanium(IV) bis(ethylacetoacetato) complex from Du Pont/Dorf Ketal

The invention claimed is:

1. A hydroxysilane of the formula (I)

$$\text{(I)}$$

where
either R' is a radical of the formula (II) and R" is hydrogen or R' is hydrogen and R" is a radical of the formula (II);

2. A hydroxysilane as claimed in claim 1, wherein $R^1$ and $R^2$ are either individually 2-methoxyethyl, 2-ethoxyethyl, 3-methoxypropyl, 3-ethoxypropyl, 2-(2-methoxyethoxy) ethyl, 2-octyloxyethyl, ethyl, propyl, isopropyl, butyl, isobutyl, sec-butyl, 2-ethylhexyl or N,N-dimethylaminopropyl, or together with inclusion of the nitrogen atom are an optionally substituted pyrrolidine, piperidine, hexamethyleneimine, morpholine, thiomorpholine or 4-methylpiperazine ring.

3. A hydroxysilane as claimed in claim 1, wherein $R^3$ is an ethylene radical.

4. A hydroxysilane as claimed in claim 1, wherein $R^5$ is a methyl group or an ethyl group.

5. A hydroxysilane as claimed in claim 1, wherein x is 1 or 0.

6. A process for preparing a hydroxysilane as claimed in claim 1, which comprises reacting at least one epoxysilane of the formula (III) with at least one amine of the formula (IV)

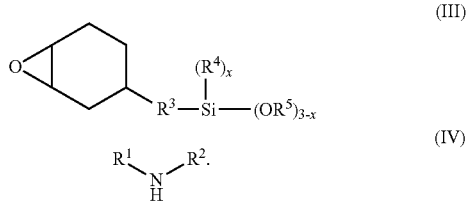

(III)

(IV)

7. An adduct obtained from the reaction of a hydroxysilane as claimed in claim 1 with at least one compound containing at least one reactive group, selected from the group consisting of isocyanate, epoxide, acryloyl, methacryloyl, anhydride, carboxylic acid, ester, carbonate and cyclocarbonate groups.

8. The adduct as claimed in claim 7, wherein it is a polymer which has end groups of the formula (VI) and is free of isocyanate groups

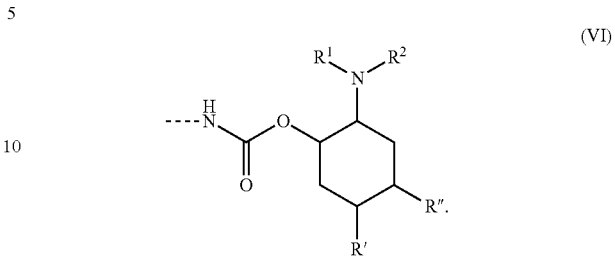

(VI)

9. The adduct as claimed in claim 8, wherein the polymer has a molecular weight in the range from 1'000 to 30'000 g/mol.

10. The adduct as claimed in claim 8, wherein the polymer has a majority of polyoxyalkylene units.

11. The adduct as claimed in claim 8, wherein a majority of the end groups of the formula (VI) are bonded to cycloaliphatic radicals.

12. The adduct as claimed in claim 8, wherein the polymer has 1 to 4 end groups of the formula (VI).

\* \* \* \* \*